United States Patent [19]

Billig et al.

[11] Patent Number: 4,605,780

[45] Date of Patent: Aug. 12, 1986

[54] REACTIVATION OF RHODIUM COMPLEX HYDROFORMYLATION CATALYSTS

[75] Inventors: Ernst Billig, Charleston; David B. Stanton, South Charleston, both of W. Va.

[73] Assignee: Union Carbide Corporation, Danbury, Conn.

[21] Appl. No.: 190,280

[22] Filed: Sep. 24, 1980

[51] Int. Cl.$^4$ .............................................. C07C 45/49
[52] U.S. Cl. .................... 568/454; 568/449; 568/451; 585/848; 260/429
[58] Field of Search .............. 568/454, 449, 451; 260/921, 429; 585/848; 252/416

[56] References Cited

U.S. PATENT DOCUMENTS

| | | | |
|---|---|---|---|
| 3,527,809 | 9/1970 | Pruett | 568/454 |
| 3,555,098 | 1/1971 | Olivier et al. | 568/454 |
| 4,148,830 | 4/1979 | Pruett et al. | 568/454 |
| 4,193,942 | 3/1980 | Gerritsen et al. | 568/454 |
| 4,196,096 | 4/1980 | Dawes et al. | 252/414 |
| 4,221,743 | 9/1980 | Halstead et al. | 568/454 |
| 4,238,419 | 12/1980 | Matsumoto et al. | 568/454 |
| 4,242,284 | 12/1980 | Harris et al. | 568/454 |
| 4,247,486 | 1/1981 | Brewester et al. | 568/454 |
| 4,260,828 | 4/1981 | Morrell et al. | 568/454 |
| 4,283,304 | 8/1981 | Bryant at al. | 568/454 |

FOREIGN PATENT DOCUMENTS 51-23212 2/1976 Japan .

*Primary Examiner*—Richard L. Raymond
*Assistant Examiner*—Raymond Covington
*Attorney, Agent, or Firm*—Reynold J. Finnegan

[57] ABSTRACT

Process for removing alkyl substituted phosphine from a hydroformylation medium and enhancing the rhodium complex catalyst contained therein via an oxygenation treatment.

14 Claims, No Drawings

REACTIVATION OF RHODIUM COMPLEX HYDROFORMYLATION CATALYSTS

FIELD OF THE INVENTION

This invention relates to a process for selectively converting alkyl substituted phosphine present in a hydroformylation reaction medium to its corresponding phosphine oxide, while at the same time improving the activity of the rhodium complex hydroformylation catalyst contained in said medium.

BACKGROUND OF THE INVENTION

Processes for forming an aldehyde by the hydroformylation reaction of an olefinic compound with carbon monoxide and hydrogen in the presence of a rhodium complex hydroformylation catalyst and free triarylphosphine are well known in the art and of particular importance are those hydroformylation reactions designed to produce aldehyde products rich in their normal isomers at significantly low pressures, such as taught for example in U.S. Pat. Nos. 3,527,809 and 4,148,830 and commonly assigned copending U.S. patent application Ser. No. 776,934, filed Mar. 11, 1977, now U.S. Pat. No. 4,260,828 (Belgium Pat. No. 853,377).

It is also known that the rhodium complex catalyst loses activity (i.e. becomes partially deactivated) during prolonged use and thus reactivation of such partially deactivated catalysts is of extreme importance to the state of the art due to the high cost of rhodium values. While it is difficult to ascertain all of the reasons for such an activity loss it is believed that in large scale hydroformylation reactions that the loss in activity is due at least in part to the presence of alkyl substituted phosphine in the hydroformylation medium. For instance it is known that the presence of alkyldiarylphosphine in the rhodium complex catalyzed hydroformylation of the alpha-olefin, propylene, inhibits catalyst productivity, i.e. the rate at which the desired product aldehydes are formed. It is further known that when triarylphosphine ligand is employed in the hydroformylation of an alpha-olefin, alkyldiarylphosphine is produced in situ, the "alkyl" group thereof normally being derived from the alpha-olefin undergoing hydroformylation and the "aryl" groups thereof being the same as the aryl of the triarylphosphine and that in a continuous hydroformylation reaction of alpha-olefins in the presence of triarylphosphine ligand to produce aldehydes, the continued build-up of such alkyl substituted phosphines can eventually lead to an unacceptable decrease in the rate of reaction and activity of the rhodium complex catalyst due to the affinity of such alkyl substituted phosphines for the catalyst.

Commonly assigned U.S. patent application Ser. No. 762,335 filed Jan. 25, 1977 (Belgium Pat. No. 863,267) now abandoned in favor of continuation application Ser. No. 140,830 filed Apr. 16, 1980, now U.S. Pat. No. 4,260,828 suggests utilizing the stability effect that alkyldiarylphosphine has on the rhodium catalyst of such hydroformylation reactions by adjusting the reaction conditions to be more severe in order to regain the loss in catalyst productivity, while retaining catalytic activity due to the enhanced catalyst stability attributed to the presence of such alkyldiarylphosphine. However such a procedure is not a totally adequate solution to maintaining the productivity of the catalyst solution.

Commonly assigned U.S. patent application Ser. Nos. 040,913 and 108,279 filed May 21, 1979, now abandoned and Dec. 28, 1979, now U.S. Pat. No. 4,283,304 respectively both disclose a method for removing undesirable alkyl substituted phosphine from a liquid composition containing a rhodium hydroformylation catalyst by treating said composition in the presence of water with an alpha,beta-unsaturated compound or anhydride thereof, e.g. maleic acid or its anhydride, so as to form solubilized reaction products with the phosphines present in said composition and removing said products by phase separation. Such a procedure, while beneficial to improving hydroformylation activity, is not without the obvious drawbacks attendant with any phase separation and washing operation.

Additional methods that have been suggested for reactivating the rhodium catalyst of a hydroformylation reaction include the following.

U.S. Pat. No. 3,555,098 relates to maintaining or improving the rhodium catalytic activity of a hydroformylation reaction by washing all or a portion of a liquid medium containing the catalyst with an aqueous solution, e.g. an aqueous alkaline solution, to remove by-product acid, e.g. carboxylic acid, formed during hydroformylation by oxidation of the aldehyde which may have been due to oxygen contamination of the reactant gas stream.

Japanese Patent Application Publication No. 23,212/76 relates to maintaining or improving the rhodium catalytic activity of a hydroformylation reaction by removing the aldehyde from the distilled reaction product mixture containing the catalyst and then treating all or a portion of the liquid catalyst medium with oxygen during the recycling procedure of the catalyst back to the hydroformylation reaction.

U.S. Pat. No. 4,196,096 relates to a method for regenerating rhodium hydroformylation catalysts which comprises the steps of removing all or a portion of the inactive catalyst from the hydroformylation reaction, adjusting the aldehyde content so as to have at least one mole of aldehyde per mole of rhodium and ligand (e.g. triphenylphosphine) present and treating the aldehyde containing catalyst with oxygen or an oxygen containing gas at a temperature less than the boiling point of the aldehyde, removing any solid material formed during oxidation and adjusting the ligand to rhodium ratio as required for use in the hydroformylation reaction.

U.S. Pat. No. 4,221,743 relates to a hydroformylation process wherein the rate of productivity of the process can be maintained at a desired rate by feeding a sufficient amount of oxygen during the hydroformylation reaction to the homogeneous liquid phase composition of the reaction so as to maintain or increase the activity of the rhodium catalyst.

Note that U.S. Pat. Nos. 3,555,098 and 4,196,096 and said Japanese reference all teach that their reactivation procedure is carried out in a different vessel than the hydroformylation reactor and that none of the references discuss the detrimental effect of alkyl substituted phosphine in the hydroformylation reaction medium. Moreover, while the invention of above-mentioned U.S. Pat. No. 4,221,743 is carried out in the hydroformylation reactor vessel, said invention relates to a procedure conducted during the hydroformylation reaction and under hydroformylation conditions and also does not discuss the detrimental effect of alkyl substituted phosphine in the hydroformylation medium.

SUMMARY OF THE INVENTION

It has now been discovered that the activity of a rhodium complex hydroformylation catalyst that has become at least partially deactivated from its employment in a continuous hydroformylation reaction can be improved and that undesirable alkyl substituted phosphine by-product present in the hydroformylation reaction medium can be selectively converted to its corresponding non-detrimental phosphine oxide.

Thus it is an object of this invention to provide a process for improving the activity of a rhodium complex hydroformylation catalyst that has become at least partially deactivated. It is another object of this invention to provide a simultaneous method for selectively converting alkyl substituted phosphine by-product present in the hydroformylation reaction medium to its corresponding phosphine oxide. Other objects and advantages of this invention will become readily apparent from the following description and appended claims.

Accordingly, the generic aspect of this invention can be described as a process for converting alkyl substituted phosphine by-product to its corresponding phosphine oxide and improving the activity of a rhodium complex hydroformylation catalyst contained in a hydroformylation reaction medium, which catalyst has become partially deactivated from its employment in a continuous hydroformylation reaction to produce aldehyde products by reacting an olefinic compound, carbon monoxide and hydrogen in the presence of a hydroformylation reaction medium contained in a reaction vessel, said process comprising stopping the hydroformylation reaction being conducted in said vessel and treating, under non-hydroformylation conditions, all or a proportionate part of the hydroformylation reaction medium derived therefrom which consists essentially of from about 5 to about 60 percent by weight of aldehyde products, from about 10 to about 70 percent by weight of higher boiling aldehyde condensation by-products, a partially deactivated soluble rhodium complex hydroformylation catalyst in an amount sufficient to provide a rhodium concentration in said derived medium of from about 25 ppm to about 1200 ppm of rhodium calculated as free metal, from about 0.1 to about 5 percent by weight of free alkyl substituted phosphine by-product of the formula

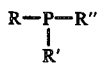 (I)

wherein R is an alkyl radical, R' is an alkyl or aryl radical and R" is an aryl radical, and from about 5 to about 25 percent by weight of free triarylphosphine ligand, said above mentioned weight percentages being based on the total weight of said derived hydroformylation reaction medium, with a sufficient amount of oxygen or oxygen containing gas for a sufficient period of time, at a temperature of from about 20° C. to about 80° C., until at least about 25 percent by weight of said alkyl substituted phosphine has been converted to its alkyl substituted phosphine oxide, while converting less than about 50 percent by weight of said triarylphosphine ligand to its triarylphosphine oxide.

DESCRIPTION OF THE PREFERRED EMBODIMENTS

The particular continuous hydroformylation process for producing aldehydes from which the hydroformylation reaction medium employed in the present invention may be derived, as well as the reaction conditions and ingredients of said hydroformylation process are not narrowly critical features of the present invention, since such serves only as a means for supplying the hydroformylation reaction medium to be treated with oxygen or an oxygen containing gas according to the present invention. Thus while the hydroformylation reaction mediums to be treated according to this invention may be derived from any suitable continuous hydroformylation process, in general the preferred hydroformylation reaction mediums employable in the present invention are those hydroformylation reaction mediums derived from the continuous hydroformylation procedures taught in said U.S. Pat. No. 4,148,830 and said U.S. patent application Ser. No. 776,934, the disclosures of which are incorporated herein by reference thereto. Said references disclose continuous liquid and gas recycle hydroformylation processes wherein an olefinic compound is reacted with carbon monoxide and hydrogen in a reaction vessel and in the presence of a hydroformylation reaction medium consisting essentially of a liquid homogeneous mixture containing aldehyde products, higher boiling aldehyde condensation by-products, a soluble rhodium complex hydroformylation catalyst, and free triarylphosphine; which medium may also eventually contain free alkyl substituted phosphine byproduct as a result of its in situ buildup in the continuous process.

In such continuous hydroformylation reactions in which aldehyde products are constantly being recovered, the hydroformylation reaction mediums of such reactions still retain a substantial amount of aldehyde products during the reaction, the amount of which can be governed by the feed of the olefinic compound, hydrogen and carbon monoxide and other reaction conditions as explained in said U.S. Pat. No. 4,148,830 and said Ser. No. 776,934, and which may range from about 5 percent to about 60 percent by weight of said aldehyde products based on the total weight of said hydroformylation reaction medium. Thus the particular aldehyde products that are present in the hydroformylation reaction medium to be treated according to this invention will obviously correspond to those aldehyde products produced by the particular continuous hydroformylation reaction from whence said medium to be treated is derived. Preferably such aldehyde products are mixtures rich in their normal to isomer ratio, i.e., contain at least about four moles of normal aldehyde product per mole of isomeric aldehyde product. For example, the continuous hydroformylation of propylene produces butyraldehyde products, which products under preferred operational conditions are rich in their normal to isomer ratio. Of course, the particular aldehyde products contained in a given hydroformylation reaction medium to be treated according to this invention will depend upon the particular olefinic compound employed in the continuous hydroformylation reaction from whence said medium to be treated is derived. Said aldehyde products, of course, each contain one more carbon atom than the olefinic compound employed in the hydroformylation reaction. Olefinic compounds that may be employed in such hydroformylation reactions include those containing from 2 to 20 carbon atoms and which may contain groups or substituents that do not essentially interfere with the course of the hydroformylation reaction and the process of this invention, such as generically taught in the prior art, especially U.S. Pat. No. 3,527,809. Illustrative olefinic compounds include alkenes such as alpha olefins and internal olefins, alkyl alkenoates, alkenyl alkanoates, alkenyl alkylethers, alkenols, and the like. The preferred olefinic compounds are alpha-olefins containing from 2 to 20 carbon atoms and more preferably from 2 to 6 carbon atoms, such as ethylene, propylene, 1-butylene, 1-pentylene, 1-hexylene, and the like. The process of this invention is especially useful for treating a hydroformylation reaction medium derived from the continuous hydroformylation of propylene to form butyraldehydes having a high normal to isomer ratio, as disclosed in said Ser. No. 776,934.

While the amount of aldehyde products contained in the hydroformylation reaction medium to be treated according to this invention will also be dependent upon the particular continuous hydroformylation reaction employed from whence said medium to be treated is derived and may range from about 5 percent to about 60 percent by weight based on the total weight of said derived medium, more preferably said derived medium contains from about 10 to about 30 percent by weight of aldehyde products based on the total weight of said derived medium. Thus in continuous hydroformylation reactions that may retain more than 30 percent by weight of aldehyde products in their hydroformylation reaction mediums during said reactions, it is preferred to reduce the amount of such retained aldehyde products prior to stopping the hydroformylation reaction that is being conducted in the reaction vessel, and/or treating the hydroformylation reaction mediums derived therefrom according to this invention, such that said derived hydroformylation mediums will contain only from about 10 to about 30 percent by weight of aldehyde products based on the total weight of the derived medium. Such may be accomplished by any suitable method such as by sufficiently lowering the temperature and pressure of the reaction vessel while maintaining its cycle flow, so as to remove mainly only the desired amount of excess aldehyde products and to minimize the loss of any of the other components contained in the hydroformylation reaction medium. While the purpose of removing excess aldehyde product is largely economical, i.e., the recovery of additional desired aldehyde product, its removal also serves the purpose of minimizing the amount of carboxylic acid that may be formed during the oxidation treatment of this invention, as well as being an oxidative safety consideration that is recommended herein.

The free alkyl substituted phosphine by-product (i.e. that amount alkyl substituted phosphine by-product that is not complexed with or tied to the rhodium complex hydroformylation catalyst) present in the hydroformylation reaction medium to be treated according to this invention, and which can be selectively converted to its corresponding phosphine oxide by this invention, may be any phosphine of the type shown by Formula I above.

For instance, as noted above, when a triarylphosphine ligand is employed in the continuous hydroformylation of an olefinic compound some alkyl substituted phosphine by-product, such as shown by Formula I above, may be produced in situ, the "alkyl" group(s) thereof normally being derived from the olefinic compound undergoing hydroformylation and the "aryl" group(s) thereof normally corresponding to the aryl radical of the triarylphosphine ligand. For example, the continuous hydroformylation of propylene by the preferred procedure described in said Ser. No. 776,934 leads to the in situ formation of propyldiphenylphosphine, as well as some detectable butyldiphenylphosphine. Thus the alkyl substituted phosphine by-product present in the hydroformylation reaction mediums to be treated according to this invention may consist of mixtures of one or more such alkyl substituted phosphines. Dialkylarylphosphines which may also possibly be present as a result of in situ formation can also be converted to their corresponding phosphine oxides by the process of this invention. Accordingly the alkyl radical of said alkyl substituted phosphine may be any alkyl radical containing from 2 to 20 carbon atoms and may be straight or branched-chained and may contain groups or substituents which do not essentially interfere with the process of this invention. Note however, that it is not applicants' intention to be bound by any precise discussion or explanation of how said alkyl substituted phosphines are formed in situ, it being sufficient for the purpose of this invention to simply point out that their in situ formation is possible and that such alkyl substituted phosphines can be converted to their corresponding oxides when present in the hydroformylation reaction medium by the oxidative treatment of said medium according to this invention.

Thus the particular free alkyl substituted phosphine by-product, as well as its amount, present in a given hydroformylation reaction medium to be treated according to this invention will obviously correspond to and merely be dependent upon the particular alkyl substituted phosphine by-product that has been formed in situ and the amount accumulated in the particular hydroformylation reaction medium from whence the hydroformylation reaction medium to be treated according to this invention has been derived. In general the amount of free alkyl substituted phosphine by-product present in the hydroformylation medium to be treated according to this invention may range from 0.1 to about 5 percent by weight and more preferably ranges from about 0.2 to about 2.5 percent by weight, based on the total weight of said medium.

The free triarylphosphine ligand (i.e. that amount triarylphosphine that is not complexed with or tied to the rhodium complex hydroformylation catalyst) present in the hydroformylation reaction medium to be treated according to this invention can be any triarylphosphine ligand suitable for use in continuous hydroformylation reactions, such as taught by said U.S. Pat. Nos. 3,527,809 and 4,148,830 and said Ser. No. 776,934.

Illustrative triarylphosphine ligands include triphenylphosphine, trinaphthylphosphine, tritolylphosphine, tri(p-biphenyl) phosphine, tri(p-methoxyphenyl) phosphine, p-(N,N-dimethylamino)phenyl diphenylphosphine, and the like.

Thus the particular free triarylphosphine ligand, as well as its amount, present in a given hydroformylation reaction medium to be treated according to this invention will obviously correspond to and merely be dependent upon the particular free triarylphosphine ligand that has been employed in the particular continuous hydroformylation reaction from whence the hydroformylation reaction medium to be treated according to this invention has been derived. Triphenylphosphine is presently the preferred triarylphosphine ligand. Accordingly in general the amount of free triarylphosphine ligand present in the hydroformylation reaction medium to be treated according to this invention may range from about 5 percent by weight to about 25 percent by weight, preferably from about 8 percent by weight to about 15 percent by weight, based on the total weight of said medium to be treated. Moreover, in preferred continuous hydroformylation reactions particularly advantageous results are achieved when the amount of free triarylphosphine ligand in the hydroformylation reaction medium of such reactions is at least about 100 moles of free triarylphosphine per mole of catalytically active rhodium metal present in the rhodium complex hydroformylation catalyst. Thus the preferred hydroformylation reaction medium to be treated according to this invention will also generally contain at least about 100 moles of free triarylphosphine ligand per mole of catalytically active rhodium metal present in the rhodium complex hydroformylation catalyst of said hydroformylation reaction medium to be treated according to this invention.

The partially deactivated rhodium complex hydroformylation catalyst, present in the hydroformylation reaction medium to be treated according to this invention can be any rhodium hydroformylation catalyst suitable for use in continuous hydroformylation reactions, such as taught by said U.S. Pat. Nos. 3,527,809 and 4,148,830 and said Ser. No. 776,934, and which has been employed in the continuous hydroformylation reaction to the extent that it has become partially deactivated i.e. does not have the same rate of activity of corresponding fresh rhodium complex catalyst.

Thus the particular partially deactivated rhodium complex hydroformylation catalyst, as well as its amount, present in a given hydroformylation reaction medium to be treated according to this invention will obviously correspond to and merely be dependent upon the particular rhodium complex hydroformylation catalyst employed in and/or formed under the reaction conditions of the continuous hydroformylation reaction from whence the hydroformylation reaction medium to be treated according to this invention has been derived. For example, as seen by the preferred operational features taught in U.S. Pat. Nos. 3,527,809 and 4,148,830 and said Ser. No. 776,934, the preferred hydroformylation reaction mediums contain a rhodium complex catalyst consisting essentially of rhodium complexed with carbon monoxide and triarylphosphine (corresponding to the free triarylphosphine ligand also contained in said medium). As noted above, as the hydroformylation reaction continues, alkyl substituted phosphine of formula (I) above is formed in situ, the amount of which continues to build up over the period of time that the continuous hydroformylation reaction is operational. Said alkyl substituted phosphine ligand having a greater affinity for rhodium than triarylphosphine may also tie or bind itself to the rhodium thereby resulting in a rhodium complex catalyst consisting essentially of rhodium complexed with carbon monoxide, triarylphosphine ligand and/or said alkyl substituted phosphine ligand (i.e. either one or both of said triarylphosphine ligand and said alkyl substituted phosphine ligand). Moreover, it is to be understood that the rhodium complex catalyst terminology "consisting essentially of", as employed herein, is not meant to exclude, but rather include the likely possibility of alkyl substituted phosphine and hydrogen complexed with the rhodium in addition to carbon monoxide and triarylphosphine, the hydrogen being derived from the hydrogen gas of the hydroformylation reaction if not already present in the catalyst precursor.

As pointed out in the above discussed prior art the rhodium complex hydroformylation complex catalyst may be formed in situ during the hydroformylation reaction or preformed by methods known in the art. For example preformed rhodium hydridocarbonyl-tris (triphenylphosphine) may be introduced into the reaction medium of the hydroformylation reaction. Alternatively rhodium catalyst precursors such as rhodium carbonyl triphenylphosphine acetylacetonate, $Rh_2O_3$, $Rh_4(CO)_{12}$, $Rh_6(CO)_{16}$, $Rh(NO_3)_3$ or rhodium dicarbonyl acetylacetonate, and the like, may be introduced into the reaction medium of the hydroformylation reaction. In either event an active rhodium complex hydroformylation catalyst is formed in the hydroformylation reaction medium under the conditions of hydroformylation wherein said alkyl substituted phosphine by-product is also formed in situ. Of course it is also possible to preform a rhodium complex catalyst which contains both triarylphosphine and said alkyl substituted phosphine complexed with the rhodium if desired. Thus it is not intended to limit the present invention by any explanation as to the exact nature of the active rhodium complex hydroformylation catalyst or to the nature of the deactivated rhodium hydroformylation catalyst formed during the continuous hydroformylation reaction employed herein. clearly it is sufficient for the purpose of this invention to simply point out that carbon monoxide, triphenylphosphine, hydrogen and said alkyl substituted phosphine by-product are all ligands that are capable of being complexed with the active rhodium complex catalyst of the continuous hydroformylation reaction employed herein.

Accordingly, in general the amount of partially deactivated rhodium complex hydroformylation catalyst present in the hydroformylation reaction medium to be treated according to this invention will correspond to that catalytic amount of catalyst present in the continuous hydroformylation reaction from whence said medium to be treated has been derived, and may be that amount sufficient to provide a rhodium concentration in said medium to be treated which may range from about 25 ppm to about 1200 ppm and preferably from about 50 ppm to about 400 ppm of rhodium calculated as free metal.

Furthermore in such continuous hydroformylation reactions a substantial amount of higher boiling aldehyde condensation by-products is formed in situ during the reaction and is preferably retained in the hydroformylation reaction medium of the reaction to serve as a solvent for the rhodium complex hydroformylation catalyst as fully explained in said U.S. Pat. No. 4,148,830 and said Ser. No. 776,934. Thus the particular higher boiling aldehyde condensation by-products, as well as their amount, present in a given hydroformylation reaction medium to be treated according to this invention will obviously correspond to and merely be dependent upon the particular higher boiling aldehyde condensation by-products formed in situ and the amount accumulated in the particular hydroformylation reaction medium from whence the hydroformylation medium to be treated according to this invention has been derived. In general the amount of higher boiling aldehyde condensation by-products present in the hydroformylation medium to be treated according to this invention may range from about 10 to about 70 percent by weight and more preferably ranges from about 25 to about 60 percent by weight, based on the total weight of said medium.

More particularly this invention comprises stopping a continuous hydroformylation reaction being conducted in a reaction vessel and treating, under non-hydroformylation conditions, the hydroformylation reaction medium derived therefrom with oxygen or an oxygen containing gas until at least 25 percent by weight of the alkyl substituted phosphine by-product present in said derived medium has been converted to its alkyl substituted phosphine oxide, while at the same time converting less than about 50 percent by weight of the triarylphosphine ligand present in said derived medium to its triarylphosphine oxide. The hydroformylation reaction can obviously be stopped by any convenient method, such as by stopping the feed of olefinic compound, carbon monoxide and hydrogen, to the reaction vessel, allowing the residual reactants contained therein to react to completion, and shutting down the reaction being conducted in the reaction vessel. The recycle lines of the continuous reaction system can then be cleared in any conventional manner and the derived hydroformylation medium treated with oxygen or an oxygen containing gas as taught herein.

The oxidative treatment of this invention which is conducted, under non-hydroformylation conditions, i.e. while the hydroformylation reaction has been stopped as explained above, may be accomplished by adding oxygen or an oxygen containing gas to all or a proportionate part of the derived hydroformylation reaction medium in any manner which seems most convenient and suitable. Thus the method of treating the hydroformylation medium is not critical and can be accomplished simply by adding a sufficient amounts of oxygen for a sufficient period of time to obtain the desired result. For instance the oxygen or oxygen containing gas can be fed directly to and thoroughly dispersed through the hydroformylation medium while it is contained in the hydroformylation reaction vessel by introducing it into the recycle lines of the continuous hydroformylation reaction system and pumping same into said medium. While it is preferred to carry out the oxygen treatment on the entire derived medium in the same reaction vessel containing said derived medium in which the hydroformylation reaction took place, if desired, the hydroformylation reaction medium to be treated can be removed from the reactor and treated in a separate vessel.

Further while it is desirable to achieve an improvement in the activity of the hydroformylation medium that will approach the activity of fresh rhodium complex catalyst, it is preferred to balance such an improvement against the amount of triarylphosphine that might also be converted to its oxide. Thus in the subject invention it is considered that in most instances the use of sufficient oxygen or an oxygen containing gas for a sufficient period of time to convert at least about 25 percent by weight, preferably at least about 50 percent by weight of the alkyl substituted phosphine to its oxide while at the same time converting less than about 50 percent by weight, preferably less than about 25 percent by weight of the triarylphosphine ligand to its oxide should be sufficient to provide satisfactory improvement in the activity of the partially deactivated catalyst. The amounts of alkyl substituted phosphine and triarylphosphine ligand converted to their oxides may be easily monitored by any conventional analytical method such as gas chromatography.

Moreover, the improved activity of the hydroformylation reaction medium so treated according to this invention may be determined by measuring the rate of reaction obtained upon employing said hydroformylation reaction medium against the rate of reaction of a similar hydroformylation reaction medium using fresh catalyst in the same manner. Of course one may also merely compare the activity of the hydroformylation medium immediately before and after it has been treated according to this invention. The difference in hydroformylation rates (or difference in catalyst activity) may then be observed in a convenient laboratory time frame such as in terms of gram-moles per liter-hour of aldehyde product produced.

While the oxidant employed in this invention is oxygen it is to be understood that oxygen need not be employed in its pure form, but more preferably and conveniently is employed in the form of an oxygen containing gas, such as air or in admixtured with an inert gas such as nitrogen in order to minimize any explosive hazards. Indeed while oxygen in the form of air is most convenient, it too may be diluted with an inert gas such as nitrogen in order to reduce its oxygen content to provide safer operating conditions when warranted. Thus it should be fully understood that when employing this invention one must be careful to avoid those conditions which could lead to the possibility of explosive detonation occurring by virtue of a large concentration of oxygen in a confined space. For example, it is highly recommended herein to thoroughly purge the hydroformylation medium and equipment system with nitrogen to remove essentially all of the reactant hydrogen gas that may be retained therein prior to the oxygen treatment of said medium. For safety reasons it is also recommended to introduce the oxygen or oxygen-containing gas into the equipment system at a point far removed from where the actual treatment is carried out, such as at a distant point in the recycle line of the continuous hydroformylation medium to give opportunity for the oxygen to mix with inerts in the system.

In view of the fact that the oxygen treatment encompassed herein is designed to convert at least about 25 percent by weight of the free alkyl substituted phosphine by-product to its phosphine oxide, but less than 50 percent by weight of the free triarylphosphine ligand to its phosphine oxide in the hydroformylation reaction medium and thereby obtain a desired improvement in the activity of the rhodium complex catalyst that has become at least partially deactivated over that obtained in the absence of such an oxygen treatment and because the components least partially deactivated over that obtained in the of the hydroformylation reaction medium can vary both in terms of their nature and concentrations, it is apparent no specific values can be arbitrarily given to conditions such as the amount and partial pressure (concentration of oxygen), temperature, and contact time for the oxygen treatment. Such conditions which may vary greatly, are not narrowly critical and obviously need only to be at least sufficient to obtain the results desired. Thus in some cases a small amount of oxygen may be more beneficial, while in other circumstances a large amount of oxygen may prove more desirable. For example, while only a small amount of oxygen may be needed in a given circumstance, it may be more desirable to use a higher concentration, and therefore a larger amount of oxygen, in order to reduce contact time. Accordingly, treatment conditions such as temperature, partial pressure (concentration) and contact time will also vary greatly and any suitable combination of such conditions may be employed herein. For instance, a decrease in any one of such conditions may be compensated for by an increase in one or both of the other conditions, while the opposite correlation is also true. In general, the oxygen may be added to the hydroformylation medium at liquid temperatures ranging from about 20° C. to about 80° C. while temperatures ranging from about 25° C. to about 60° C. should be suitable in most instances. Moreover oxygen partial pressures ranging from as little as $10^{-4}$ to 10 atmospheres should be sufficient for most purposes. Of course it is obvious that the contact time will be directly related to such conditions as temperature and oxygen concentration and may vary from a matter of seconds or minutes to hours.

Thus the subject oxygen treatment of this invention is unique in that it has been surprisingly discovered that the hydroformylation reaction medium of a continuous hydroformylation reaction can be treated all at one time and in the same reaction vessel of said reaction under mild conditions after stopping the reaction so as to selectively convert undesirable free alkyl substituted phosphine to its non-detrimental corresponding oxide despite the concurrent presence of the large excess of aldehyde product and triarylphosphine ligand also contained in said medium, and thereby improve the rate of activity of the rhodium complex catalyst that has become at least partially deactivated from said continuous reaction.

It is indeed surprising that in view of all of the possible competing reactions that may be involved with the oxygen treatment of this invention that undesirable alkyl substituted phosphine is apparently converted to its oxide faster than the conversion of triarylphosphine ligand to its oxide despite the large excess of triarylphosphine and aldehyde products present in the medium. Such a discovery allows one to control the amount of alkyl substituted phosphine and triarylphosphine contained in the hydroformylation reaction medium by selectively converting to its oxide only that amount of alkyl substituted phosphine desired, while at the same time minimizing the amount of desired triarylphosphine that will also necessarily be converted to its oxide. Moreover the subject invention furnishes one with a much wider processing latitude with regard to controlling safety considerations and in balancing the degree of improvement obtained in catalyst reactivity against the possible large loss of costly desirable components such as aldehyde product and triarylphosphine ligand as a result of their conversion to carboxylic acid and triarylphosphine oxide that may be attendant with a process such as disclosed in said U.S. Pat. No. 4,221,743 which requires its oxidative treatment to be conducted during the actual operation of the hydroformylation reaction. Furthermore, unlike prior art processes that require the addition of make-up quantities of active rhodium catalyst, solvent and/or triarylphosphine before reutilizing their treated catalyst the subject inventive process is further unique in that since the oxidation treatment of this invention can be carried out in the same reaction vessel of the hydroformylation reaction one need only turn back on the feed of olefinic compound, hydrogen and carbon monoxide to the treated hydroformylation reaction medium of this invention and restart the continuous hydroformylation reaction without the need of adding additional reaction medium components before restarting the reaction. Moreover, if one is using more than one reaction vessel in conjunction with the continuous hydroformylation reaction one need not shut off the reaction being conducted in every reaction vessel, but only the reaction that is being conducted in that reaction vessel in which the derived hydroformylation medium is to be treated. Alternatively it is to be understood that if desired, one could remove the entire hydroformylation reaction medium to be treated according to this invention from the reaction vessel of the reaction to a different vessel and then treat all or a proportionate part of said medium in said different vessel as desired. Such an optional procedure allows one to employ the empty hydroformylation reaction vessel for any other type of purpose such as for hydroformylating a different olefinic compound than employed in the initial hydroformylation reaction from which the medium to be treated has been derived. This would allow one to store the medium to be treated or the medium so treated until it is desired to be reused.

In adition it has been found that the enhanced activity of the rhodium complex catalyst obtained by the subject oxygen treatment of this invention is a sustained improvement that is not drastically reversible upon immediate use of the catalyst, but which is self-maintaining for long periods of time.

The following examples are illustrative of the present invention and are not to be regarded as limitative. It is to be understood that all of the parts, percentages and proportions referred to herein and in the appended claims are by weight unless otherwise indicated.

EXAMPLE I

A hydroformylation reaction medium was obtained from a continuous gaseous hydroformylation reaction of propylene to produce butyraldehyde, said reaction comprising feeding propylene, carbon monoxide and hydrogen to a reaction vessel and reacting same in the presence of a hydroformylation reaction medium contained therein comprising butyraldehyde products, higher boiling aldehyde condensation by-products as the solvent, free propyldiphenylphosphine, free triphenylphosphine, and a soluble rhodium complex hydroformylation catalyst consisting essentially of rhodium complexed with carbon monoxide and triphenylphosphine, said medium containing about 387 ppm rhodium (calculated as free metal) and whose catalytic activity had declined to about 30 percent of that of fresh catalyst, by shutting off the reactant feed gases, stopping the hydroformylation reaction and stripping essentially all (more than 99.5%) of said reactant gases from the reaction vessel and cycle lines. Analysis of the hydroformylation reaction medium so obtained showed it to contain about 14 percent by weight of butyraldehyde products, about 63 percent by weight of higher boiling aldehyde condensation by-products, about 0.9 percent by weight of free propyldiphenylphosphine, and about 17 percent by weight of free triphenylphosphine, the remainder consisting essentially of said rhodium complex catalyst, triphenylphosphine oxide and higher boiling organic components, e.g. aldehyde pentamers.

Said derived hydroformylation reaction medium was then oxygenated while present in the same reaction vessel by passing a gaseous air-nitrogen mixture (about 4% oxygen) through said medium for about 14 hours, at about 70° C., about 58 p.s.i.g., and at an average feed flow rate of about 10.1 standard cubic feet of gas per hour per gallon of said derived medium to obtain an oxygenated treated hydroformylation reaction medium containing about 8 percent by weight of butyraldehyde products, about 0.05 percent by weight of free propyldiphenylphosphine and about 13 percent by weight of free triphenylphosphine, in addition to the other components mentioned above and present in said medium before said oxygen treatment. Said analysis indicates that about 94 percent by weight of the original free propyldiphenylphosphine was oxidized to its corresponding phosphine oxide while only about 23 percent by weight of the original free triphenylphosphine was oxidized to its corresponding phosphine oxide by said oxygen treatment.

A resumed continuous gaseous hydroformylation reaction of propylene to produce butyraldehyde employing the oxygenated hydroformylation reaction medium so obtained, showed it to have a catalytic activity rating of about 85 percent after about four days of operation which leveled off to a catalytic activity rating of about 50 percent for the second week of continuous operation, as compared to the activity of fresh rhodium complex catalyst under the same conditions.

EXAMPLE II

A hydroformylation reaction medium was obtained from a continuous gaseous hydroformylation reaction of propylene to produce butyraldehyde, said reaction comprising feeding propylene, carbon monoxide and hydrogen to a reaction vessel and reacting same in the presence of a hydroformylation reaction medium contained therein comprising butyraldehyde products, higher boiling aldehyde condensation by-products as the solvent, free propyldiphenylphosphine, free triphenylphosphine, and a soluble rhodium complex hydroformylation catalyst consisting essentially of rhodium complexed with carbon monoxide and triphenylphosphine, said medium containing about 183 ppm rhodium (calculated as free metal) and whose catalytic activity had declined to about 40 percent of that of fresh catalyst, by shutting off the reactant feed gases, stopping the hydroformylation reaction and stripping essentially all (more than 99.5%) of said reactant gases from the reaction vessel and cycle lines. Analysis of the hydroformylation reaction medium so obtained showed it to contain about 22 percent by weight of butyraldehyde products, about 65 percent by weight of higher boiling aldehyde condensation by-products, about 0.3 percent by weight of free propyldiphenylphosphine, and about 11 percent by weight of free triphenylphosphine, the remainder consisting essentially of said rhodium complex catalyst, triphenylphosphine oxide and higher boiling organic components, e.g. aldehyde pentamers.

Said derived hydroformylation reaction medium was then oxygenated while present in the same reaction vessel by passing a gaseous air-nitrogen mixture (about 4% oxygen) through said medium for about 13 hours, at about 60° to 67° C., about 60 p.s.i.g., and at an average feed flow rate of about 13.2 standard cubic feet of gas per hour per gallon of said derived medium to obtain an oxygenated treated hydroformylation reaction medium containing about 16 percent by weight of butyraldehyde products, about 0.08 percent by weight of free propyldiphenylphosphine and about 8 percent by weight of free triphenylphosphine, in addition to the other components mentioned above and present in said medium before said oxygen treatment. Said analysis indicates that about 74 percent by weight of the original free propyldiphenylphosphine was oxidized to its corresponding phosphine oxide while only about 20 percent by weight of the original free triphenylphosphine was oxidized to its corresponding phosphine oxide by said oxygen treatment.

EXAMPLE III

A hydroformylation reaction medium was obtained from a continuous gaseous hydroformylation reaction of propylene to produce butyraldehyde, said reaction comprising feeding propylene, carbon monoxide and hydrogen to a reaction vessel and reacting same in the presence of a hydroformylation reaction medium contained therein comprising butyraldehyde products, higher boiling aldehyde condensation by-products as the solvent, free propyldiphenylphosphine, free triphenylphosphine, and a soluble rhodium complex hydroformylation catalyst consisting essentially of rhodium complexed with carbon monoxide and triphenylphosphine, said medium containing about 234 ppm rhodium (calculated as free metal) and whose catalytic activity had declined to about 40 percent of that of fresh catalyst, by shutting off the reactant feed gases, stopping the hydroformylation reaction and stripping essentially all (more than 99.5%) of said reactant gases from the reaction vessel and cycle lines. Analysis of the hydroformylation reaction medium so obtained showed it to contain about 24 percent by weight of butyraldehyde products, about 62 percent by weight of higher boiling aldehyde condensation by-products, about 0.3 percent by weight of free propyldiphenylphosphine, and about 13 percent by weight of free triphenylphosphine, the remainder consisting essentially of said rhodium complex catalyst, triphenylphosphine oxide and higher boiling organic components, e.g. aldehyde pentamers.

Said derived hydroformylation reaction medium was then oxygenated while present in the same reaction vessel by passing a gaseous air-nitrogen mixture (about 4% oxygen) through said medium for about 13 hours, at about 54° to 65° C., about 60 p.s.i.g., and at an average feed flow rate of about 14.5 standard cubic feet of gas per hour per gallon of said derived medium to obtain an oxygenated treated hydroformylation reaction medium containing about 16 percent by weight of butyraldehyde products, about 0.1 percent by weight of free propyldiphenylphosphine and about 10 percent by weight of free triphenylphosphine, in addition to the other components mentioned above and present in said medium before said oxygen treatment. Said analysis indicates that about 65 percent by weight of the original free propyldiphenyl phosphine was oxidized to its corresponding phosphine oxide while only about 11 percent by weight of the original free triphenylphosphine was oxidized to its corresponding phosphine oxide by said oxygen treatment.

EXAMPLE IV

A hydroformylation reaction medium was obtained from a continuous gaseous hydroformylation reaction of propylene to produce butyraldehyde, said reaction comprising feeding propylene, carbon monoxide and hydrogen to a reaction vessel and reacting same in the presence of a hydroformylation reaction medium contained therein comprising butyraldehyde products, higher boiling aldehyde condensation by-products as the solvent, free propyldiphenylphosphine, free triphenylphosphine, and a soluble rhodium complex hydroformylation catalyst consisting essentially of rhodium complexed with carbon monoxide and triphenylphosphine, said medium containing about 267 ppm rhodium (calculated as free metal) and whose catalytic activity had declined to about 40 percent of that of fresh catalyst, by shutting off the reactant feed gases, stopping the hydroformylation reaction and stripping essentially all (more than 99.5%) of said reactant gases from the reaction vessel and cycle lines. Analysis of the hydroformylation reaction medium so obtained showed it to contain about 25 percent by weight of butyraldehyde products, about 60 percent by weight of higher boiling aldehyde condensation by-products, about 0.4 percent by weight of free propyldiphenylphosphine, and about 14 percent by weight of free triphenylphosphine, the remainder consisting essentially of said rhodium complex catalyst, triphenylphosphine oxide and higher boiling organic components, e.g. aldehyde pentamers.

Said derived hydroformylation reaction medium was then oxygenated while present in the same reaction vessel by passing a gaseous air-nitrogen mixture (about 4% oxygen) through said medium for about 13 hours, at about 54° to 60° C., about 60 p.s.i.g., and at an average feed flow rate of about 14.7 standard cubic feet of gas per hour per gallon of said derived medium to obtain an oxygenated treated hydroformylation reaction medium containing about 16 percent by weight of butyraldehyde products, about 0.1 percent by weight of free propyldiphenyl phosphine and about 11 percent by weight of free triphenylphosphine, in addition to the other components mentioned above and present in said medium before said oxygen treatment. Said analysis indicates that about 63 percent by weight of the original free propyldiphenylphosphine was oxidized to its corresponding phosphine oxide while only about 11 percent by weight of the original free triphenylphosphine was oxidized to its corresponding phosphine oxide by said oxygen treatment.

EXAMPLE V

A resumed gaseous hydroformylation reaction of propylene to produce butyraldehyde employing the combined oxygenated reaction mediums so obtained of Examples II, III, and IV exhibited a catalytic activity rating of about 68 percent after twenty days of continuous operation as compared to the activity of fresh rhodium complex catalyst the same conditions.

Various modifications and variations of this invention will be obvious to a worker skilled in the art and it is to be understood that such modifications and variations are to be included within the purview of this application and the spirit and scope of the appended claims.

What is claimed is:

1. A process for converting alkyl substituted phosphine by-product to its corresponding phosphine oxide and improving the activity of a rhodium complex hydroformylation catalyst contained in a hydroformylation reaction medium, which catalyst has become partially deactivated from its employment in a continous hydroformylation reaction to produce aldehyde products by reacting an olefinic compound, carbon monoxide and hydrogen in the presence of a hydroformylation reaction medium contained in a reaction vessel, said process comprising stopping the hydroformylation reaction being conducted in said vessel and treating, under nonhydroformylation conditions, all or a proportionate part of the hydroformylation reaction medium derived therefrom which consists essentially of from about 5 to about 60 percent by weight of aldehyde products, from about 10 to about 70 percent by weight of higher boiling aldehyde condensation by-products, a partially deactivated soluble rhodium complex hydroformylation catalyst in an amount sufficient to provide a rhodium concentration in said derived medium of from about 25 ppm to about 1200 ppm of rhodium calculated as free metal, from about 0.1 to about 5 percent by weight of free alkyl substituted phosphite by-product of the formula

wherein R is an alkyl radical, R' is an alkyl or aryl radical and R" is an aryl radical, and from about 5 to about 25 percent by weight of free triarylphosphine ligand, said above mentioned weight percentages being based on the total weight of said derived hydroformylation reaction medium, with a sufficient amount of oxygen or oxygen containing gas for a sufficient period of time, at a temperature of from about 20° C. to about 80° C., until at least about 50 percent by weight of said alkyl substituted phosphine has been converted to its alkyl substituted phosphine oxide, while converting less than about 25 percent by weight of said triarylphosphine ligand to its triarylphosphine oxide.

2. A process as defined in claim 1, wherein said derived hydroformylation medium to be treated contains from about 10 to about 30 percent by weight of aldehyde products.

3. A process as defined in claim 1, wherein said derived hydroformylation medium to be treated contains from about 25 to about 60 percent by weight of higher boiling aldehyde condensation by-products.

4. A process as defined in claim 1 wherein the olefinic compound is an alpha-olefin containing from 2 to 20 carbon atoms.

5. A process as defined in claim 1 wherein said derived hydroformylation reaction medium contains from about 0.2 to about 2.5 percent by weight of free alkyl substituted phosphine.

6. A process as defined in claim 5 wherein the free alkyl substituted phosphine is propyldiphenylphosphine.

7. A process as defined in claim 1, wherein said derived hydroformylation medium contains from about 8 to about 15 percent by weight of free triarylphosphine.

8. A process as defined in claim 7, wherein said triarylphosphine is triphenylphosphine.

9. A process as defined in claim 1, wherein the oxidative treatment of the derived hydroformylation medium is conducted at a temperature of from about 25° C. to about 60° C.

10. A process as defined in claim 1, wherein the oxidative treatment of the derived hydroformylation medium is conducted in the same reaction vessel of the hydroformylation process from whence said medium is derived.

11. A process as defined in claim 1, wherein air or an air-nitrogen mixture is employed as the source of oxygen for the oxidative treatment of said derived hydroformylation medium.

12. A process as defined in claim 1, wherein said derived hydroformylation medium to be treated contains from about 10 to about 30 percent by weight of butyraldehyde products, wherein the free alkyl substituted phosphine is propyldiphenylphosphine, wherein the free triarylphosphine is triphenylphosphine, where the oxidative treatment of the derived hydroformylation medium is conducted at a temperature of from about 25° C. to about 60° C. and wherein at least about 50 percent by weight of said propyldiphenylphosphine is converted to its propyldiphenylphosphine oxide, while converting less than 25 weight percent of said triphenylphosphine to its triphenylphosphine oxide.

13. A process as defined in claim 12, wherein the oxidative treatment of the derived hydroformylation medium is conducted in the same reaction vessel of the hydroformylation process from whence said medium is derived.

14. A process as defined in claim 13, wherein air or an air-nitrogen mixture is employed as the source of oxygen for the oxidative treatment of said derived hydroformylation medium.

* * * * *